(12) United States Patent
Norton et al.

(10) Patent No.: US 10,172,849 B2
(45) Date of Patent: Jan. 8, 2019

(54) COMPOSITIONS COMPRISING BUPRENORPHINE

(71) Applicant: Indivior UK Limited, Slough (GB)

(72) Inventors: Richard L. Norton, Fort Collins, CO (US); Mingxing Zhou, Fort Collins, CO (US)

(73) Assignee: INDIVIOR UK LIMITED, Slough (GB)

( * ) Notice: Subject to any disclaimer, the term of this patent is extended or adjusted under 35 U.S.C. 154(b) by 0 days.

(21) Appl. No.: 15/060,184

(22) Filed: Mar. 3, 2016

(65) Prior Publication Data

US 2016/0184296 A1 Jun. 30, 2016

Related U.S. Application Data

(63) Continuation of application No. 13/703,015, filed as application No. PCT/GB2011/051058 on Jun. 6, 2011, now Pat. No. 9,295,645.

(51) Int. Cl.

| | | |
|---|---|---|
| A61K 31/48 | (2006.01) | |
| A61K 31/485 | (2006.01) | |
| A61K 9/00 | (2006.01) | |
| A61K 9/10 | (2006.01) | |
| A61K 47/10 | (2017.01) | |
| A61K 47/26 | (2006.01) | |
| A61K 31/439 | (2006.01) | |

(Continued)

(52) U.S. Cl.
CPC .......... *A61K 31/485* (2013.01); *A61K 9/0019* (2013.01); *A61K 9/08* (2013.01); *A61K 9/10* (2013.01); *A61K 9/16* (2013.01); *A61K 9/1682* (2013.01); *A61K 31/439* (2013.01); *A61K 47/10* (2013.01); *A61K 47/26* (2013.01); *B65B 3/003* (2013.01); *B65B 55/08* (2013.01); *B65B 55/16* (2013.01)

(58) Field of Classification Search
None
See application file for complete search history.

(56) References Cited

U.S. PATENT DOCUMENTS

| | | | |
|---|---|---|---|
| 3,466,362 | A | 9/1969 | Klaui et al. |
| 4,534,974 | A | 8/1985 | Kim |

(Continued)

FOREIGN PATENT DOCUMENTS

| | | |
|---|---|---|
| EP | 0 368 409 A2 | 5/1990 |
| EP | 0 368 409 A3 | 5/1990 |

(Continued)

OTHER PUBLICATIONS

Aird, J. (Apr. 2003). Controlled Release—SMi Conference. Feb. 12-13, 2003, London,UK, *IDrugs* 6(4):334-336.

(Continued)

*Primary Examiner* — Robert A Wax
*Assistant Examiner* — Melissa S Mercier
(74) *Attorney, Agent, or Firm* — Mintz Levin Cohn Ferris Glovsky and Popeo, P.C.

(57) ABSTRACT

This disclosure relates to a buprenorphine sustained release delivery system for treatment of conditions ameliorated by buprenorphine compounds. The sustained release delivery system includes a flowable composition containing a suspension of buprenorphine, a metabolite, or a prodrug thereof.

18 Claims, 3 Drawing Sheets

(51) Int. Cl.
*A61K 9/08* (2006.01)
*A61K 9/16* (2006.01)
*B65B 3/00* (2006.01)
*B65B 55/08* (2006.01)
*B65B 55/16* (2006.01)

(56) References Cited

U.S. PATENT DOCUMENTS

| | | |
|---|---|---|
| 4,573,995 A | 3/1986 | Chen et al. |
| 4,599,354 A | 7/1986 | Shulman |
| 4,626,539 A | 12/1986 | Aungst et al. |
| 4,755,389 A | 7/1988 | Jones et al. |
| 4,784,855 A | 11/1988 | Yamashita et al. |
| 4,804,663 A | 2/1989 | Kennis et al. |
| 4,938,763 A | 7/1990 | Dunn et al. |
| 5,008,110 A | 4/1991 | Benecke et al. |
| 5,026,556 A | 6/1991 | Drust et al. |
| 5,069,909 A | 12/1991 | Sharma et al. |
| 5,096,715 A | 3/1992 | Sinclair |
| 5,173,304 A | 12/1992 | Lohner et al. |
| 5,324,519 A | 6/1994 | Dunn et al. |
| 5,346,903 A | 9/1994 | Ackerman et al. |
| 5,453,425 A | 9/1995 | Francois et al. |
| 5,486,362 A | 1/1996 | Kitchell et al. |
| 5,616,587 A | 4/1997 | Francois et al. |
| 5,648,093 A | 7/1997 | Gole et al. |
| 5,688,801 A | 11/1997 | Mesens et al. |
| 5,702,716 A | 12/1997 | Dunn et al. |
| 5,744,153 A | 4/1998 | Yewey et al. |
| 5,770,231 A | 6/1998 | Mesens et al. |
| 5,780,044 A | 7/1998 | Yewey et al. |
| 5,792,477 A | 8/1998 | Rickey |
| 5,948,787 A * | 9/1999 | Merrill ............... A61K 9/0004 514/282 |
| 5,990,194 A | 11/1999 | Dunn et al. |
| 6,004,969 A | 12/1999 | Hu |
| 6,120,789 A | 9/2000 | Dunn |
| 6,224,905 B1 | 5/2001 | Lawrence et al. |
| 6,261,583 B1 | 7/2001 | Dunn et al. |
| 6,264,987 B1 | 7/2001 | Wright et al. |
| 6,284,274 B1 | 9/2001 | Merrill et al. |
| 6,294,192 B1 | 9/2001 | Patel et al. |
| 6,303,137 B1 | 10/2001 | Dittgen et al. |
| 6,355,657 B1 | 3/2002 | Osborne |
| 6,383,471 B1 | 5/2002 | Chen et al. |
| 6,395,293 B2 | 5/2002 | Polson et al. |
| 6,413,536 B1 | 7/2002 | Gibson et al. |
| 6,528,080 B2 | 3/2003 | Dunn et al. |
| 6,565,874 B1 | 5/2003 | Dunn et al. |
| 6,596,316 B2 | 7/2003 | Lyons et al. |
| 6,630,155 B1 | 10/2003 | Chandrashekar et al. |
| 7,041,320 B1 | 5/2006 | Nuwayser |
| 7,410,635 B2 | 8/2008 | Blondino et al. |
| 7,501,113 B2 * | 3/2009 | Blondino ............. A61K 9/0078 128/200.14 |
| 7,691,408 B2 | 4/2010 | Leroux et al. |
| 8,114,383 B2 | 2/2012 | Bartholomaus et al. |
| 8,114,429 B2 | 2/2012 | Michal et al. |
| 8,133,507 B2 | 3/2012 | Yum et al. |
| 8,173,148 B2 | 5/2012 | Dadey et al. |
| 8,221,778 B2 | 7/2012 | Siegel et al. |
| 8,236,755 B2 | 8/2012 | Thuresson et al. |
| 8,257,722 B2 | 9/2012 | Michal et al. |
| 8,313,763 B2 | 11/2012 | Margaron et al. |
| 8,324,343 B2 | 12/2012 | Moore et al. |
| 8,329,203 B2 | 12/2012 | Siegel et al. |
| 8,333,989 B2 | 12/2012 | Sukuru |
| 8,377,479 B2 | 2/2013 | Talton |
| 8,415,401 B2 | 4/2013 | Yum et al. |
| 8,512,749 B2 | 8/2013 | Sawhney et al. |
| 8,563,023 B2 | 10/2013 | Michal et al. |
| 8,574,552 B2 | 11/2013 | Stroppolo et al. |
| 8,586,103 B2 | 11/2013 | Li et al. |
| 8,815,944 B2 | 8/2014 | Leroux et al. |
| 8,852,638 B2 | 10/2014 | Luk et al. |
| 8,877,241 B2 | 11/2014 | Fischer et al. |
| 8,916,202 B2 | 12/2014 | Lebon et al. |
| 8,921,387 B2 | 12/2014 | Norton et al. |
| 8,975,270 B2 | 3/2015 | Norton et al. |
| 9,017,709 B2 | 4/2015 | Griguol et al. |
| 9,044,450 B2 | 6/2015 | Luk et al. |
| 9,168,216 B2 | 10/2015 | Gavin et al. |
| 9,221,831 B2 | 12/2015 | Kyle et al. |
| 9,254,268 B2 | 2/2016 | Krayz et al. |
| 9,259,872 B2 | 2/2016 | Hayes et al. |
| 9,272,044 B2 | 3/2016 | Norton et al. |
| 9,295,645 B2 | 3/2016 | Norton et al. |
| 9,308,162 B2 | 4/2016 | Norton |
| 9,326,979 B2 | 5/2016 | Kimura et al. |
| 9,364,518 B2 | 6/2016 | Nadkarni et al. |
| 9,415,034 B2 | 8/2016 | Oliver et al. |
| 9,468,599 B2 | 10/2016 | Ray, II et al. |
| 9,498,432 B2 | 11/2016 | Norton et al. |
| 9,555,226 B2 | 1/2017 | Zumbrunn et al. |
| 9,597,402 B2 | 3/2017 | Luk et al. |
| 2003/0004100 A1 | 1/2003 | Dasch et al. |
| 2003/0068375 A1 | 4/2003 | Wright et al. |
| 2003/0129219 A1 | 7/2003 | Hong et al. |
| 2003/0211157 A1 | 11/2003 | Simon |
| 2004/0018238 A1 | 1/2004 | Shukla |
| 2004/0033250 A1 | 2/2004 | Patel et al. |
| 2004/0101557 A1 | 5/2004 | Gibson et al. |
| 2004/0138237 A1 | 7/2004 | Shah |
| 2004/0151670 A1 | 8/2004 | Blondino et al. |
| 2005/0032781 A1 | 2/2005 | Ehrich |
| 2005/0048115 A1 | 3/2005 | Mangena et al. |
| 2005/0048123 A1 | 3/2005 | Su et al. |
| 2005/0053647 A1 | 3/2005 | Matusch et al. |
| 2005/0112067 A1 | 5/2005 | Kumar et al. |
| 2006/0002979 A1 | 1/2006 | Ashammakhi et al. |
| 2006/0003008 A1 | 1/2006 | Gibson et al. |
| 2006/0210604 A1 | 9/2006 | Dadey et al. |
| 2007/0077304 A1 | 4/2007 | Luk et al. |
| 2007/0117828 A1 | 5/2007 | Simmons et al. |
| 2007/0265190 A1 | 11/2007 | Thuresson et al. |
| 2008/0020011 A1 | 1/2008 | Finkelstein et al. |
| 2008/0020039 A1 | 1/2008 | Parikh et al. |
| 2008/0299168 A1 | 12/2008 | Dadey et al. |
| 2009/0048145 A1 | 2/2009 | Hellerbrand et al. |
| 2009/0061011 A1 * | 3/2009 | Talton .................. A61K 9/5021 424/501 |
| 2009/0074708 A1 | 3/2009 | Oliver et al. |
| 2009/0092650 A1 | 4/2009 | Warren et al. |
| 2009/0202481 A1 | 8/2009 | Li et al. |
| 2009/0246265 A1 | 10/2009 | Stinchcomb et al. |
| 2010/0098735 A1 | 4/2010 | Jain et al. |
| 2010/0173940 A1 | 7/2010 | Leichs et al. |
| 2010/0266655 A1 | 10/2010 | Dadey |
| 2010/0292195 A1 | 11/2010 | Dadey et al. |
| 2010/0330150 A1 | 12/2010 | Venkatesh et al. |
| 2011/0229526 A1 | 9/2011 | Rosenberg et al. |
| 2011/0230816 A1 | 9/2011 | Copp-Howland |
| 2012/0058158 A1 | 3/2012 | Booles |
| 2012/0207843 A1 | 8/2012 | Lebon et al. |
| 2013/0023553 A1 | 1/2013 | Jude-Fishburn et al. |
| 2013/0129828 A1 | 5/2013 | Talton |
| 2013/0143909 A1 | 6/2013 | Chong et al. |
| 2013/0177603 A1 | 7/2013 | Gutierro Aduriz et al. |
| 2013/0202658 A1 | 8/2013 | Norton et al. |
| 2013/0210751 A1 | 8/2013 | Dong et al. |
| 2013/0231359 A1 | 9/2013 | Chong et al. |
| 2013/0331803 A1 | 12/2013 | Fleschhut et al. |
| 2014/0023692 A1 | 1/2014 | Du Toit et al. |
| 2014/0134261 A1 | 5/2014 | Singh et al. |
| 2014/0271869 A1 | 9/2014 | Richey et al. |
| 2014/0363487 A1 | 12/2014 | Hille et al. |
| 2015/0209555 A1 | 7/2015 | Ruane et al. |
| 2015/0231258 A1 | 8/2015 | Luk et al. |
| 2015/0359891 A1 | 12/2015 | Chen et al. |
| 2016/0303038 A1 | 10/2016 | Yadav et al. |

(56) References Cited

U.S. PATENT DOCUMENTS

| | | |
|---|---|---|
| 2017/0079974 A1 | 3/2017 | Zhou et al. |
| 2017/0079976 A1 | 3/2017 | Norton et al. |

FOREIGN PATENT DOCUMENTS

| | | |
|---|---|---|
| EP | 0 532 546 A1 | 3/1993 |
| EP | 0 532 546 B1 | 3/1993 |
| EP | 0 572 494 A1 | 12/1993 |
| EP | 0 572 494 B1 | 12/1993 |
| EP | 1 006 935 A1 | 6/2000 |
| EP | 1 006 935 B1 | 6/2000 |
| EP | 1 015 032 A2 | 7/2000 |
| EP | 1 644 002 A1 | 4/2006 |
| EP | 1 644 002 B1 | 4/2006 |
| EP | 1 830 900 A1 | 9/2007 |
| EP | 1 940 351 A2 | 7/2008 |
| EP | 1 940 351 B1 | 7/2008 |
| EP | 2 081 574 A1 | 7/2009 |
| EP | 2 361 609 A1 | 8/2011 |
| EP | 2 361 609 B1 | 8/2011 |
| EP | 2 445 487 A2 | 5/2012 |
| EP | 2 797 602 | 11/2014 |
| GB | 784659 A | 10/1957 |
| GB | 806876 | 1/1959 |
| GB | 873526 A | 7/1961 |
| GB | 887872 A | 1/1962 |
| IN | 1535/DEL/2004 | 8/2006 |
| WO | WO-1991/19474 A1 | 12/1991 |
| WO | WO-93/23019 A1 | 11/1993 |
| WO | WO-95/27481 A1 | 10/1995 |
| WO | WO-96/21427 A1 | 7/1996 |
| WO | WO-96/39095 A1 | 12/1996 |
| WO | WO-98/58685 A1 | 12/1998 |
| WO | WO-00/06117 A1 | 2/2000 |
| WO | WO-00/024374 A1 | 5/2000 |
| WO | WO-01/15699 A1 | 3/2001 |
| WO | WO-01/35929 A2 | 5/2001 |
| WO | WO-01/35929 A3 | 5/2001 |
| WO | WO-02/30393 A2 | 4/2002 |
| WO | WO-02/30393 A3 | 4/2002 |
| WO | WO-02/038185 A2 | 5/2002 |
| WO | WO-02/038185 A3 | 5/2002 |
| WO | WO-2004/037259 A1 | 5/2002 |
| WO | WO-2003/041684 A2 | 5/2003 |
| WO | WO-2003/041684 A3 | 5/2003 |
| WO | WO-2004/043432 A2 | 5/2004 |
| WO | WO-2004/043432 A3 | 5/2004 |
| WO | WO-2006/041942 A2 | 4/2006 |
| WO | WO-2006/041942 A3 | 4/2006 |
| WO | WO-2006/053175 A2 | 5/2006 |
| WO | WO-2006/053175 A3 | 5/2006 |
| WO | WO-2007/041410 A2 | 4/2007 |
| WO | WO-2007/041410 A3 | 4/2007 |
| WO | WO-2007/061828 A2 | 5/2007 |
| WO | WO-2007/061828 A3 | 5/2007 |
| WO | WO-2007/103185 A2 | 9/2007 |
| WO | WO-2007/103185 A3 | 9/2007 |
| WO | WO-2008/045516 A1 | 4/2008 |
| WO | WO-2008/100532 A1 | 8/2008 |
| WO | WO-2008/153611 A2 | 12/2008 |
| WO | WO-2008/153611 A3 | 12/2008 |
| WO | WO-2009/091737 A2 | 7/2009 |
| WO | WO-2009/091737 A3 | 7/2009 |
| WO | WO-2011/154724 A2 | 12/2011 |
| WO | WO-2011/154724 A3 | 12/2011 |
| WO | WO-2011/154724 A9 | 12/2011 |
| WO | WO-2011/154725 A2 | 12/2011 |
| WO | WO-2011/154725 A3 | 12/2011 |
| WO | WO-2014/016428 A1 | 1/2014 |
| WO | WO-2014/081343 A2 | 5/2014 |
| WO | WO-2014/081343 A3 | 5/2014 |
| WO | WO-2015/136253 A1 | 9/2015 |

OTHER PUBLICATIONS

Astaneh, R. et al. (Jan. 2009). "Changes in morphology of in situ forming PLGA implant prepared by different polymer molecular weight and its effect on release behavior," J Pharm Sci 98(1):134-145.

Baker, D.L. et al. (Oct. 2004). "Gonadotropin-releasing hormone agonist: a new approach to reversible contraception in female deer," J Wildl Dis 40(4):713-724.

Bartsch, W. et al. (1976). "Acute Toxicity in Various Solvents in the Mouse and Rat," Arzneim-Forsch, Drug Res 26:1581-1583.

Basu, S.K. et al. (Mar. 2004). "Protein crystals for the delivery of biopharmaceuticals," Expert Opin Biol Ther 4(3):301-317.

Becci, P.J. et al. (1983). "Subchronic feeding study in beagle dogs of N-methylpyrrolidone," J Appl Toxicol 3(2):83-86.

Berges, R. et al. (2005). "Eligard®: Pharmacokinetics, effect on Testosterone and PSA Levels and Tolerability," European Urology Supplements 4:20-25.

Boongird, A. et al. (Jan. 2011). "Biocompatibility study of glycofurol in rat brains," Exp Biol Med 236(1):77-83.

Bowersock, T.L. et al. (1999). "Vaccine delivery to animals," Adv Drug Deliv Rev 38(2):167-194.

Bromberg, L.E. et al. (Jul. 31, 2000). "Sustained release of silver from periodontal wafers for treatment of periodontitis," J Control Release 68(1):63-72.

Chandrashekar, B.L. et al. (Jul. 1999). "Sustained Release of Leuprolide Acetate from an In-situ Forming Biodegradable Polymeric Implant as the Delivery Vehicle," Proceed Int'l Symp Control Rel Bioact Mater 26, 3 pages.

Chen, F.A. et al. (Jul. 2003). "Biodegradable polymer-mediated intratumoral delivery of cisplatin for treatment of human head and neck squamous cell carcinoma in a chimeric mouse model," Head Neck 25(7):554-560.

Chu, F.M. et al. (Sep. 2002). "A clinical study of 22.5 mg. La-2550: A new subcutaneous depot delivery system for leuprolide acetate for the treatment of prostate cancer," Journal of Urology 168(3):1199-1203.

Contet C, Kieffer BL, Befort K. Mu opioid receptor: a gateway to drug addiction. Curr Opin Neurobiol 14:370-378, 2004.

Coonts, B.A. et al. (Oct. 1993). "Plasma Concentrations of Naltrexone Base Following Subcutaneous and Intramuscluar Injections of Atrigel™ Formulations in Dogs," Pharmaceutical Research: Official Journal of the American Association of Pharmaceutical Scientists PHREEB 10(10):PDD 7071, 2 pages.

Cox, M.G. et al. (Aug. 2005). "Leuprolide acetate given by a subcutaneous extended-release injection: less of a pain?" Expert Rev Anticancer Ther 5(4):605-611.

Crawford, E.D. et al. (Feb. 2006). "A 12-month clinical study of LA-2585 (45.0 mg): a new 6-month subcutaneous delivery system for leuprolide acetate for the treatment of prostate cancer," Journal of Urology 175(2):533-536.

Dadey, E.J. (2008). The Atrigel Drug Delivery System. In: Rathbone et al Eds, Modified-Release Drug Delivery Technology, 2nd Ed., New York, pp. 183-190.

Dernell, W.S. et al. (1998). "Apparent interaction of dimethyl sulfoxide with cisplatin released from polymer delivery devices injected subcutaneously in dogs," J Drug Target 5(5):391-396.

Domb, A.J. et al. (1989). "Solid-State and Solution Stability of Poly(anhydrides) and Poly(esters)," Macromolecules 22(5):2117-2122.

Dunn, R.S., (2003). "The Atrigel Drug Delivery System," Modified-Release Drug Delivery Technology, Edited by Rathbone, Hadgraft, Roberts, Marcel Dekker, Inc., Chapter 54, pp. 647-655.

Dunn, R.L. et al. (1996). "Sustained Release of Cisplatin in Dogs from an Injectable Implant Delivery System," Journal of Bioactive and Compatible Polymers, 11:286-300.

Duysen, E.G. et al (1992). "Bioactivity of Polypeptide Growth Factors Released from the ATRIGEL Drug Delivery System," PHREEB, 9(10):S73, Abstract No. 2028.

Duysen, E.G. et al (1993). "Release of Bioactive Growth Factors from the ATRIGEL Delivery System in Tibial Defect and Dermal Wound Models," PHREEB, 10(10):583, Abstract No. 2043.

(56) References Cited

OTHER PUBLICATIONS

Duysen, E.G. et al (1994). "An Injectable, Biodegradable Delivery System for Antineoplastic Agents," *PHREEB*, 11(10):S88, Abstract No. 2071.
Eliaz, R.E. et al. (Dec. 2000). "Delivery of soluble tumor necrosis factor receptor from in-situ forming PLGA implants: in-vivo," *Pharm Research* 17(12):1546-1550.
Erickson, N.M. et al. (2001). "An in Vitro Degradation Study Comparing Poly (DL-Lactide-Co-Glycolide) with Acid End Groups and Ester End Groups," $20^{th}$ Southern Biomedical Engineering Conference, 1 page.
Evans, H.C., et al (2004). "Leuprorelin: Subcutaneous Depot Formulation (ELIGARD) for Advanced Prostate Cancer," *Am J. Cancer*, 3(3):197-201.
FDA Document K982865 (1998). Atrix Laboratories, Inc. 13 pages.
FDA Document K994137 (2000). Atrix Laboratories, Inc. 9 pages.
Frank, K.R. et al (1994). "Controlled Release of Bioactive Growth Factors from a Biodegradable Delivery System," PHREEB, 11(10):S88, Abstract No. 2070.
Frost, J.J., Wagner, H.N. Jr., Dannals, R.F., Ravert, H.T., Links, J.M., Wilson, A.A., Burns, H.D., Wong, D.F., McPherson, R.W., Rosenbaum, A.E., Kuhar, M.J. & Snyder, S.H. (1985). Imaging opiate receptors in the human brain by positron tomography. *J Comp Assist Tomogr*, 9, 231-236.
Gerentes, P. et al. (2002). "Study of a chitin-based gel as injectable material in periodontal surgery," *Biomaterials* 23(5):1295-1302.
Graves, R.A. et al. (Aug. 3, 2007). "In vitro dissolution method for evaluation of buprenorphine in situ gel formulation: a technical," *AAPS PharmSciTech* 8(3): Article 62, E1-E4.
Greenwald MK, Johanson CE, Moody DE, Woods JH, Kilbourn MR, Koeppe RA, Schuster CR, Zubieta JK (2003) *Neuropsychopharmacology* 28: 2000-2009.
Greenwald MK, Johanson CE, Bueller J, Chang Y, Moody DE, Kilbourn MR, Koeppe RA, Zubieta JK (2007) Buprenorphine duration of action: Mu-opioid receptor availability, pharmacokinetic and behavioral indices. *Biological Psychiatry* 61: 101-110.
Griffeth, R.J. et al. (2002). "Is Lucteal Production of $PGF_2\alpha$ Required for Luteolysis?" *Biology of Reproduction* 66(Supplement 1), Abstract 465, 2 pages.
Hempel, G. et al. (May 1, 2007). "Cytotoxicity of dimethylacetamide and pharmacokinetics in children receiving intravenous busulfan," *J Clin Oncol* 25(13)1772-1778.
Jain, R.A. (Dec. 2000). "The manufacturing techniques of various drug loaded biodegradable poly(lactide-co-glycolide) (PLGA) devices," *Biomaterials* 21(23):2475-2490.
Jarr, E.M. et al. (Jul. 1999). "Sustained Release of Lidocaine from an Injectable Implant System for Treatmenr of Post-Operative," *Proceedings Int'l Symp Control Rel Bioact Materials* Abstract #5423, 4 pages.
Johnson, O.L. et al. (Jun. 1997). "The stabilization and encapsulation of human growth hormone into biodegradable microspheres," Pharm res 14(6):730-735.
Kaul, S. et al. (Feb. 2000). "Polymeric-based perivascular delivery of a nitric oxide donor inhibits intimal thickening after balloon denudation arterial injury: role of nuclear factor-kappaB," *J Am Coll Cardiol* 35(2):493-501.
Kissel, T. (Jan. 2002). "ABA-triblock copolymers from biodegradable polyester A-blocks and hydrophilic poly(ethylene oxide) B-blocks as a candidate for in situ forming hydrogel delivery systems for proteins," *Adv Drug Deily Rev* 54(1):99-134.
Kranz, H. et al. (Jan. 5, 2001). "Myotoxicity studies of injectable biodegradable in-situ forming drug delivery systems," *Int J Pharm* 212(1):11-18.
Lee, K.P. et al. (Aug. 1987). "Toxicity of N-methyl-2-pyrrolidone (NMP): teratogenic, subchronic, and two-year inhalation studies," *Fundam Appl Toxicol* 9(2):222-235.
Lester PA, Traynor JR. Comparison of the in vitro efficacy of mu, delta, kappa and ORL1 receptor agonists and non-selective opioid agonists in dog brain membranes. *Brain Res.* 2006;1073-1074:290-296.

Lewis JW., Buprenorphine. Drug Alcohol Depend. 1985; 14:363-372.
Li, M. et al. (Nov. 2003). "A novel, non-prostanoid EP2 receptor-selective prostaglandin E2 agonist stimulates local bone formation and enhances fracture healing," *Bone Miner Res* 18(11):2033-2042.
Liao, C-L. et al. (2008). "In vitro skin permeation of buprenorphine transdermal patch," Journal of Food and Drug Analysis 16(6):8-15.
Lindhardt et al, "Intranasal Absorption of Buprenorphine—in vivo biovavailability study in sheep." Int. J. Pharm., 205(1-2):159-163 (2000).
Ling W, Wesson DR, Charuvastra C, Klett CJ. A controlled trial comparing buprenorphine and methadone maintenance in opioid dependence. *Arch. Gen. Psychiatry.* 1996; 53:401-407.
Ling W, Charuvastra C, Collins JF, Batki S, Brown LS, Jr, Kintaudi P, Wesson Dr, McNicholas L, Tusel DJ, Malkerneker U, Renner JA, Jr, Santos E, Casadonte P, Fye C, Stine S, Wang RI, Segal D. Buprenorphine maintenance treatment of opiate dependence: a multicenter, randomized clinical trial. *Addiction.* 1998; 93:475-486.
Lutfy K, Cowan A. Buprenorphine: a unique drug with complex pharmacology. *Curr. Neuropharmacol.* 2004; 2:395-402.
Lynch, G.S. et al. (Nov. 204). "Emerging drugs for sarcopenia: age-related muscle wasting," *Expert Opin Emerg Drugs* 9(2);345-361.
Makadia, H.K. et al. (Sep. 1, 2011, e-published Aug. 26, 2011). "Poly Lactic-co-Glycolic Acid (PLGA) as Biodegradable Controlled Drug Delivery Carrier," *Polymers* 3(3):1377-1397.
Malik, K. et al. (2010). "Atrigel: A Potential Parenteral Controlled Drug Delivery System," *Der Pharmacia Sinica* 1(1):74-81.
Matschke, C. et al. (Dec. 2007). "Sustained-release injectables formed in situ and their potential use for veterinary products," *J Control Release* 85(1-3):1-15.
Matthes HW, Maldonado R, Simonin F, Valverde O, Slowe S, Kitchen I, Befort K, Dierich A, Le Meur M, Dolle P, Tzavara E, Hanoune J, Rogues BP, Kieffer BL. Loss of morphine-induced analgesia, reward effect and withdrawal symptoms in mice lacking the mu-opioid-receptor gene. *Nature* 1996; 383:819-823.
McLeod, D.G. et al. (Feb. 2003). "Hormonal therapy: historical perspective to future directions," *Urology* 61(2 Suppl 1):3-7.
Mealy (2004). "Treatment of Metabolic Disorders by Condition," Annual Update 2003/2004—*Drugs of the Future* 29(8):843-872.
Medicott, N.J. et al. (Jun. 23, 2004). "Sustained release veterinary parenteral products," *Adv Drug Deliv Rev* 56(10):1345-1365.
Miller, R.A. et al. (Sep. 1977). "Degradation rates of oral resorbable implants (polylactates and polyglycolates): rate modification with changes in PLA/PGA copolymer ratios," *Biomed Mater Res* 11(5):711-719.
Mottu, F. et al. (Apr. 2000). "In vitro assessment of new embolic liquids prepared from preformed polymers and water-miscible solvents for aneurysm treatment," *Biomaterials* 21(8):803-811.
Packhaeuser, C.B. et al. (Sep. 2004). "In situ forming parenteral drug delivery systems: an overview," *Eur J Pharm Biopharm* 58(2):445-455.
Panaccione, C. et al. (1997). "Use of a Trinomial Distribution Probability Model in Development of a Tier-Testing Scheme for Content Uniformity Testing," *Drug Information Journal* 31:903-909.
Paralkar, V.M. et al. (May 27, 2003, e-published May 14, 2003). "An EP2 receptor-selective prostaglandin E2 agonist induces bone healing," *PNAS USA* 100(11):6736-6740.
Parent, M. et al. (Nov. 28, 2013, e-published Sep. 1, 2013). "PLGA in situ implants formed by phase inversion: critical physicochemical parameters to modulate drug release," *J Control Release* 172(1):292-304.
Patel, R.B. et al. (Nov. 1, 2010, e-published Aug. 20, 2010). "Effect of injection site on in situ implant formation and drug release in vivo," *J Control Release* 147(3):350-358.
Pechenov, S. et al. (Apr. 16, 2004). "Injectable controlled release formulations incorporating protein crystals," *J Control Release* 96(1):149-158.
Perez-Merreno, R. (Nov. 2002). "A six-month, open-label study assessing a new formulation of leuprolide 7.5 mg for suppression of testosterone in patients with prostate cancer," *Clinical Therapuetics* 24(11):1902-1914.

(56) References Cited

OTHER PUBLICATIONS

Perez-Marrero, R. et al. (Feb. 2004). "A subcutaneous delivery system for the extended release of leuprolide acetate for the treatment of prostate cancer," *Expert Opin Pharmacother* 5(2):447-457.
Radomsky, M.L. et al. (1993). "The Controlled Release of Ganirelix from the Atrigel™ Injectable Implant System," Proceed Intern *Symp Control Rel Bioact Mater* 20:458-459.
Rathbone, M.J. et al. (Aug. 1, 2002). "Modified release drug delivery in veterinary medicine," *Drug Discov Today* 7(15):823-829.
Ravivarapu, H.B. et al. (Feb. 28, 2000). "Sustained activity and release of leuprolide acetate from an in situ forming polymeric implant," *AAPS PharmSciTech* 1(1):E1.
Ravivarapu, H.B. et al. (Jun. 2000). "Sustained suppression of pituitary-gonadal axis with an injectable, in situ forming implant of leuprolide acetate," *J Pharm Sci* 89(6):732-741.
Ravivarapu, H.B. et al. (Jan. 25, 2000). "Parameters affecting the efficacy of a sustained release polymeric implant of leuprolide," *Int J Pharm* 194(2):181-191.
Schoenhammer, K. et al. (Apr. 17, 2009, e-published Dec. 24, 2008). "Injectable in situ forming depot systems: PEG-DAE as novel solvent for improved PLGA storage stability," *Int J. Pharm* 371(1-2):33-39.
Schoenhammer, K. et al. (Dec. 2009, e-published Oct. 1, 2009). "Poly(ethyleneglycol) 500 dimethylether as novel solvent for injectable in situ forming depots," *Pharm Res* 26(12):2568-2577.
Schulman, C.C. (2005). "LHRH Agonists in Prostate Cancer Optimising Testosterone Control with Eligard®," *European Urology Supplements* 4:1-3.
Schwach-Abdellaoui, K. et al. (Jul. 2000). "Local delivery of antimicrobial agents for the treatment of periodontal diseases," *Eur J Pharm Biopharm* 50(1):83-99.
Sherman, J.M. et al. (1994). "Localized Delivery of Bupivacaine HCL from Astrigel™ Formulations for the Management of Postoperative Pain," *Pharmaceutical Research* 11(10), PDD7574, 2 pages.
Sigmon et al, "An injection depot formulation of buprenorphine: extended biodelivery and effects," Addiction, 101:420-432 (2006).
Sinha, V.R. et al. (Jun. 18, 2004). "Poly-epsilon-caprolactone microspheres and nanospheres: an overview," *Int J. Pharm* 278(1):1-23.
Smith, R.W. et al. (2004). "A Study of Water Diffusion, in Both Radial and Axial Directions, into Biodegradable Monolithic Depots Using Ion Beam Analysis," *Polymer* 45:4893-4908.
Sobel et al, "Open-label trial of an injection depot formulation of buprenorphine in opioid detoxification," Drug and Alcohol Dependence, 73:11-22 (2004).
Southard, G.L. et al. (Feb. 1998). "Subgingival controlled release of antimicrobial agents in the treatment of periodontal disease," *Int J Antimicrob Agents* 9(4):239-253.
Southard, G.L. et al. (Sep. 1998). "The drug delivery and biomaterial attributes of the ATRIGEL® technology in the treatment of periodontal disease," *Expert Opin Investig Drugs* 7(9):1483-1491.
Sundaram, S. et al. (2004). "Peptides: Nasal and Pulmonary Delivery of Deslorelin, a Peptide Drug," *American Pharmaceutical Review* 130-139.
Swanson, B.N. (Jan.-Jun. 1985). "Medical use of dimethyl sulfoxide (DMSO)," *Rev Clin Basic Pharm* 5(1-2):1-33.
Tipton, A.J. et al. (Oct. 1991). "A Biodegradable, Injectable Delivery System for NonSteroidal Anti-Flammatory Drugs," *Pharmaceutical Research* 8(10), PDD 7279, 2 pages.
Titeler, M., Lyon, R.A., Kuhar, M.J., Frost, J.J., Dannals, R.F., Leonhardt, S., Bullock, A., Rydelek, L.T., Price, D.L. & Struble, R.G. (1989). Mu opiate receptors are selectively labeled by [3H]-carfentanil in human and rat brain. *Eur J Pharmacol*, 167, 221-228.
Tserki, V. et al. (Feb. 2006). "Biodegradable aliphatic polyesters. Part II. Synthesis and characterization of chain extended poly(butylene succinate-co-butylene adipate)," *Polymer Degradation and Stability* 91(2):377-384.

Tunn, U.W. (Jul. 29, 2011). "A 6-month depot formulation of leuprolide acetate is safe and effective in daily clinical practice: a non-interventional prospective study in 1273 patients," *BMC Urology* 11:15.
Veilleux JC, Colvin PJ, Anderson J, York C, Heinz AJ. A review of opioid dependence treatment: pharmacological and psychosocial interventions to treat opioid addiction. *Clin Psychol Rev* 2010; 30: 155-166.
Winzenburg, G. et al. (Jun. 23, 2004). "Biodegradable polymers and their potential use in parenteral veterinary drug delivery systems," *Adv Drug Deliv Rev* 56(10):1453-1466.
Wolff, E.D. et al. (1994). "Use of Bio-Beads SM-4 Adsorbent for Bioburden Testing of Atrigel™ Biodegradable Delivery System Containing 10% Doxycycline," ASM Las Vegas 1994, Abstracts, 3 pages.
World Health Organization (2001). N-Methyl-2-Pyrrolidone, Concise International Chemical Assessment Document 35, 39 pages.
Xia, Y. et al. (Jul. 18, 2002). "Uniform biodegradable microparticle systems for controlled release," *J Control Release* 82(1):137-147.
Zhu, G. et al. (2000). "Stabilization of proteins encapsulated in cylindrical poly(lactide-co-glycolide) implants: mechanism of stabilization by basic additives," *Pharm Res* 17(3):351-357.
International Preliminary report on Patentability dated Jun. 29, 2016 for PCT Application No. PCT/GB2015/050676, filed Mar. 9, 2015, 18 pages.
International Search Report dated Jun. 11, 2015 for PCT Application No. PCT/GB2015/050676, filed Mar. 9, 2015, 6 pages.
Written Opinion dated Jun. 11, 2015 for PCT Application No. PCT/GB2015/050676, filed Mar. 9, 2015, 6 pages.
International Search Report and Written Opinion dated May 10, 2013 for priority application PCT/GB2011/051058.
International Preliminary Report on Patentability dated Dec. 20, 2012 for priority application PCT/GB2011/051058.
Search Report dated Oct. 6, 2010 for priority application GB1009546.1.
Ahmed, T.A. et al. (Oct. 2012, e-published Jun. 29, 2012). "Development of biodegradable in situ implant and microparticle injectable formulations for sustained delivery of haloperidol," *J Pharm Sci* 101(10):3753-3762.
Ahmed, T.A. et al. (Jun. 2015, e-published Mar. 20, 2014). "Biodegradable injectable in situ implants and microparticles for sustained release of montelukast: in vitro release, pharmacokinetics, and stability," *AAPS PharmSciTech* 15(3):772-780.
Babu, R.J. et al. (May-Jun. 2005). "Effect of penetration enhancers on the transdermal delivery of bupranolol through rat skin," *Drug Deliv* 12(3):165-169.
Buggins, T.R. et al. (Dec. 22, 2007). "The effects of pharmaceutical excipients on drug disposition," *Adv Drug Deliv Rev* 59(15):1482-1503.
Cheng, Y. et al. (Dec. 2013, e-published Oct. 1, 2013). "Thermosensitive hydrogels based on polypeptides for localized and sustained delivery of anticancer drugs," *Biomaterials* 34(38):10338-10347.
Dewan, I. et al. (2011). "Study of Release Kinetics of Dexamethasone from Biodegradable PLA In-Situ Implants," *International Journal of Pharmaceutical Science and Research* 2(11):3039-3045.
Furuishi, T. et al. (Jul. 2007). "Effect of permeation enhancers on the in vitro percutaneous absorption of pentazocine," *Biol Pharm Bull* 30(7):1350-1353.
Gou, M. et al. (Apr. 2010). "Polymeric matrix for drug delivery: honokiol-loaded PCL-PEG-PCL nanoparticles in PEG-PCL-PEG thermosensitive hydrogel," *J Biomed Mater Res A* 93(1):219-226.
Ibrahim, H.M. et al. (Jan. 2014, e-published Jan. 9, 2013). "Development of meloxicam in situ implant formulation by quality by design principle," *Drug Dev Ind Pharm* 40(1):66-73.
Jaiswal, J. et al. (Mar. 1, 1999). "Transdermal delivery of naloxone: ex vivo permeation studies," *Int J Pharm* 179(1):129-134.
Kan, P. et al. (Jul. 21, 2005). "Thermogelling Emulsions for Vascular Embolization and Sustained Release Drugs," *Journal of Biomedical Materials Research* 75B(1):185-192.
Karatas, A. et al. (2006). "Studies of Release of Ketorolac Tromethamin and Indomethacin from Opthalmic Hydrogel Inserts," *Ankara Ecz Fak Derg* 35(4)255-268.

(56) References Cited

OTHER PUBLICATIONS

Kelava, T. et al. (2011). "Biological Actions of Drug Solvents," *Periodicum Biologorum* 113(3):311-320.

Lin, X. et al. (2012). "A novel risperidone-loaded SAIB-PLGA mixture matrix depot with a reduced burst release: effects of solvents and PLGA on drug release behaviors in vitro/in vivo," *J Mater Sci Mater Med* 23(2):443-455.

Madhu, M. et al. (Nov.-Dec. 2009). "Biodegradeable Injectable Implant Systems for Sustained DeliveryUsing Poly (Lactide-Co-Glycolide) Copolymers," International Journal of Pharmacy and Pharmaceutical Sciences Vol., Suppl 1, 103-107.

Mendelson, J.E. et al (Apr. 2011, e-published Dec. 8, 2010). "Lack of effect of sublingual salvinorin A, a naturally occurring kappa opioid, in humans: a placebo-controlled trial," *Psychopharmacology* 214(4):933-939.

Mownika, G. et al. (2012). "Formulation and Evaluation of Simvastatin Injectable in situ Implants," American Journal of Drug Discovery and Development 2(2):87-100.

Nahata, T. et al. (Mar.-Apr. 2009). "Formulation optimization of long-acting depot injection of aripiprazole by using D-optimal mixture design," *PDA J Pharm Sci Technol* 63(2):113-122.

Olby, N. (Sep. 2010). "The pathogenesis and treatment of acute spinal cord injuries in dogs," *Vet Clin North Am Small Anim Pract* 40(5):791-807.

Omidfar, K. et al. (2002). "Stabilization of Penicillinase-Hapten Conjugate for Enzyme Immunoassay," *Journal of Immunoassay & Immunochemistry* 23(3):385-398.

Plourde, F. et al. (Nov. 28, 2005, e-published Sep. 21, 2005). "First report on the efficacy of l-alanine-based in situ-forming implants for the long-term parenteral delivery of drugs," *J Control Release* 108(2-3):433-441.

Pluta, J. et al. (Dec. 20, 2006). "In vitro studies of the properties of thermosensitive systems prepared on Pluronic F-127 as vehicles for methotrexate for delivery to solid tumours," *Polymers in Medicine* 36(3):37-52.

Rackur, H. et al. (2001). "In-Situ Forming Implants of PLGA/Leuprolide Acetate Solutions in NMP and Their in Vitro/in Vivo Release Characteristics," 28th International Symposium on Controlled Release of Bioactive Materials and Fourth Consumer Products Conference, 2001 Proceedings, Abstract 6137, pp. 884-885.

Rafienia, M. et al. (Jul. 2007). "In Vitro Evaluation of Drug Solubility and Gamma Irradiation on the Release of Betamethasone under Simulated in Vivo Conditions," Journal of Bioactive and Compatible Polymers 22:443-459.

Reilley,K.J. et al. (Nov. 17, 2010). "Prevention of Cocaine-Conditioned Place Preference with Salvinorin a Prepared with Optimal Vehicle Conditions," 40th Annual Meeting Neuroscience 2010, Presentation Abstract, 2 pages.

Toot, J.D. et al. *International Journal of Toxicology* 32(1):66.

Wang, L. et al. (May 10, 2012, e-published Feb. 23, 2012). "Design of a long-term antipsychotic in situ forming implant and its release control method and mechanism," *Int J Pharm* 427(2):284-292.

Wischke, C. et al. (Oct. 2010, e-published Jul. 29, 2010). "Development of PLGA-based injectable delivery systems for hydrophobic fenretinide," *Pharm Res* 27(10:2063-2074.

Wu, Z. et al. (Oct. 2014, e-published Jul. 1, 2014). "Thermosensitive hydrogel used in dual drug delivery system with paclitaxel-loaded micelles for in situ treatment of lung cancer," *Colloids Surf B Biointerfaces* 122:90-98.

Yaksh, T.L. et al. (1991). "The utility of 2-hydroxypropyl-beta-cyclodextrin as a vehicle for the intracerebral and intrathecal administration of drugs," *Life Sci* 48(7):623-633.

Yang, Y. et al. (May 2012, e-published Mar. 15, 2012). "Improved initial burst of estradiol organogel as long-term in situ drug delivery implant: formulation, in vitro and in vivo characterization," *Drug Dev Ind Pharm* 38(5):550-556.

Yehia, S.A. et al. (Jun. 2012, e-published Nov. 18, 2011). "A novel injectable in situ forming poly-DL-lactide and DL-lactide/glycolide implant containing liposheres for controlled drug delivery," *J Liposome Res* 22(2):128-138.

Chemical Solution, definition of Chemical Solution by Medical Dictionary, located at <https://medical-dictionary.thefreedictionary.com/Chemical+solution> last visited Dec. 29, 2017, 10 pages.

\* cited by examiner

COMPOSITIONS COMPRISING BUPRENORPHINE

CROSS-REFERENCE TO RELATED APPLICATIONS

This application is a continuation of U.S. application Ser. No. 13/703,015 filed Feb. 5, 2013, issued as U.S. Pat. No. 9,295,645, which is a § 371 of PCT/GB2011/51058 filed Jun. 6, 2011, which claims priority to United Kingdom Application No. GB 1009546.1 filed Jun. 8, 2010.

FIELD OF THE INVENTION

This disclosure relates to a buprenorphine sustained release delivery system for treatment of conditions ameliorated by buprenorphine compounds. The sustained release delivery system includes a flowable composition containing a suspension of buprenorphine, a metabolite, or a prodrug thereof.

BACKGROUND OF THE INVENTION

Buprenorphine (also known as (2S)-2-[(−)-(5R,6R,7R,14S)-9α-cyclo-propyl-methyl-4,5-epoxy-6,14-ethano-3-hydroxy-6-methoxymorphinan-7-yl]-3,3-di-methylbutan-2-ol and marketed under the trade names SUBUTEX™ and SUBOXONE™ for relief of opioid addiction.

The chemical structure of buprenorphine is shown in formula (1).

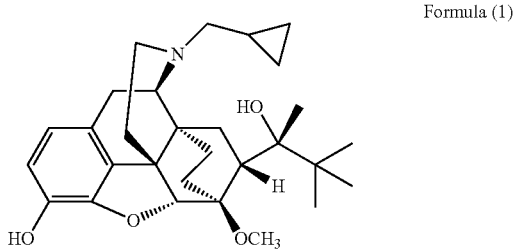 [SMILES: CO[C@]12CC[C@@]3(C[C@@H]1[C@](C)(O)C(C)(C)C)[C@H]1Cc4ccc(O)c5c4[C@@]3(CCN1CC1CC1)[C@H]2O5]

Formula (1)

Buprenorphine is most often used to treat symptoms arising from opioid addiction and for the long term relief of pain. Currently, the commercial opioid addiction products are SUBUTEX™ and SUBOXONE™ marketed by RB Pharma Inc. These products are in a tablet formulation and are intended to deliver therapeutic levels of buprenorphine for short periods of time of up to several hours and are typically taken either buccally or sublingually. However, the patient is required to supplement this dose at regular intervals, and there are often issues with diversion in patients with an opioid dependence problem. There is a need therefore for a longer term, non-divertible method of administering buprenorphine which delivers a constant and effective dose of the active to the patient over a period of up to 30 days, and which does not result in an unwanted accumulation of residual active in the patient's metabolism.

Various sustained release methods are employed in the pharmaceutical industry, for example, systems such as solid, biodegradable rods, or nondegradable reservoirs. These, however, typically require surgical implantation and furthermore, for the nondegradable delivery systems, a second surgical procedure is required to remove the empty reservoir.

There is a continuing need to develop products providing increased bioavailability of buprenorphine. In particular, there is a need to develop sustained release formulations of buprenorphine that do not suffer from low bioavailability, poor release kinetics, injection site toxicity, relatively large volume injections, and inconveniently short duration of release.

SUMMARY OF THE INVENTION

The present invention is directed to a buprenorphine sustained release delivery system capable of delivering buprenorphine, a metabolite, or a prodrug thereof for a duration of about 7 days to about 1 month. The buprenorphine sustained release delivery system includes a flowable composition for the sustained release of buprenorphine, a metabolite, or a prodrug thereof. The buprenorphine sustained release delivery system provides at least 7 days and up to 30 days release profiles characterized by an exceptionally high bioavailability and minimal risk of permanent tissue damage and typically no risk of muscle necrosis.

Surprisingly, it has been found that such a sustained release delivery system is achieved by a composition comprising a suspension of buprenorphine in water, wherein the buprenorphine is in particulate form.

Accordingly, there is provided according to the first embodiment of the present invention, a composition comprising a suspension of 5-20 wt % of buprenorphine in water; and, a polyethylene glycol (PEG) polymer, wherein the buprenorphine is in particulate form with an average particle size of less than 200μ; and, the composition does not comprise a polylactide or polyglycolide polymer or mixture thereof.

Preferably, the average particle size of the buprenorphine in the composition as hereinbefore described is less than 150μ, preferably less than 120μ, preferably less than 100μ, preferably less than 80μ, preferably less than 60μ, preferably less than 50μ, preferably less than 40μ.

Especially preferably, the average particle size of the buprenorphine in the composition as hereinbefore described is less than 20μ, more especially preferably less than 10μ.

In one preferred embodiment, the composition as hereinbefore described comprises buprenorphine present as the free base (unprotonated) form.

In another preferred embodiment, the composition as hereinbefore described comprises buprenorphine present as a protonated salt form.

In a further preferred embodiment, the composition as hereinbefore described further comprises a water soluble polymer selected from the group consisting of polyethylene glycols (PEG), carboxymethylcelluloses (CMC), polyvinylpyrrolidones (PVP), polyvinylalcohols (PVA) and dextrans.

In a yet further embodiment, there is provided a composition as hereinbefore described wherein the water soluble polymer is a PEG, preferably wherein the PEG has a MW of between 1000 to 10,000.

In a yet further embodiment, there is provided a composition according to any preceding claim which further comprises a nonionic surfactant selected from the group consisting of Tween 20, Tween 80, poloxamers and phospholipids, preferably wherein the surfactant is one or both of Tween 20 or Tween 80.

In a yet further embodiment, there is provided a composition according to any preceding claim further comprising pharmaceutically acceptable salts or sugars to adjust the tonicity of the composition, and/or preservatives, preferably selected from the group consisting of methylparaben, propylparaben and benzylalcohol.

In a second embodiment of the present invention, there is provided a method of treating a patient for opioid dependence or pain relief comprising administering parenterally and extravascularly a composition substantially as hereinbefore described according to the first embodiment of the present invention.

Preferably, the method according to the second embodiment provides treatment for opioid dependence or pain relief over a period of at least 7 days.

Preferably, the method according to the second embodiment provides treatment for opioid dependence or pain relief over a period of no more than 30 days.

In a particular preference, the method of treating a patient according to the second embodiment provides treatment for opioid dependence or pain relief over a period of at least 7 days and no more than 28 days.

Further preferably, the method of treatment according to the second embodiment provides treatment for opioid dependence or pain relief over a period of at least 10 days and no more than 17 days.

In a further preference of the second embodiment of the invention, there is provided a method of treating a patient comprising a dosage regime of an initial dose plus follow up dosages at a regular time interval of between 7 and 30 days.

In a yet further preference of the second embodiment of the invention, there is provided a method substantially as hereinbefore described which delivers a therapeutically effective dosage of the buprenorphine, metabolite, or prodrug thereof from about 0.1 to about 10 milligrams (mg) or about 1 to about 8 milligrams (mg) per day.

In a yet further preference of the second embodiment of the invention, there is provided a method substantially as hereinbefore described wherein the dosage achieves a therapeutically effective level of the buprenorphine, metabolite, or prodrug thereof, within about one day after administration of the composition; and wherein the therapeutically effective dosage of the buprenorphine, metabolite, or prodrug thereof is delivered for at least about 7 days after administration of the composition, or for at least about 30 days after administration of the composition.

In a third embodiment of the present invention, there is provided a method of forming a composition according to the first embodiment of the invention comprising the steps of: (a) mixing the water with any further optional component, (b) add the opioid agonist along with a grinding medium, and (c) grinding the suspension until the required particle size is achieved.

In a preferred method according to the third embodiment of the present invention, the method further comprises the process of terminally sterilizing the composition, which process comprises the steps of: (a) fill the composition in pharmaceutically acceptable vials or ampoules and properly seal the vials or ampoules, and (b) terminally sterilizing the vials or ampoules by autoclaving or irradiation (gamma or electron beam).

EXAMPLES

Figure 1:
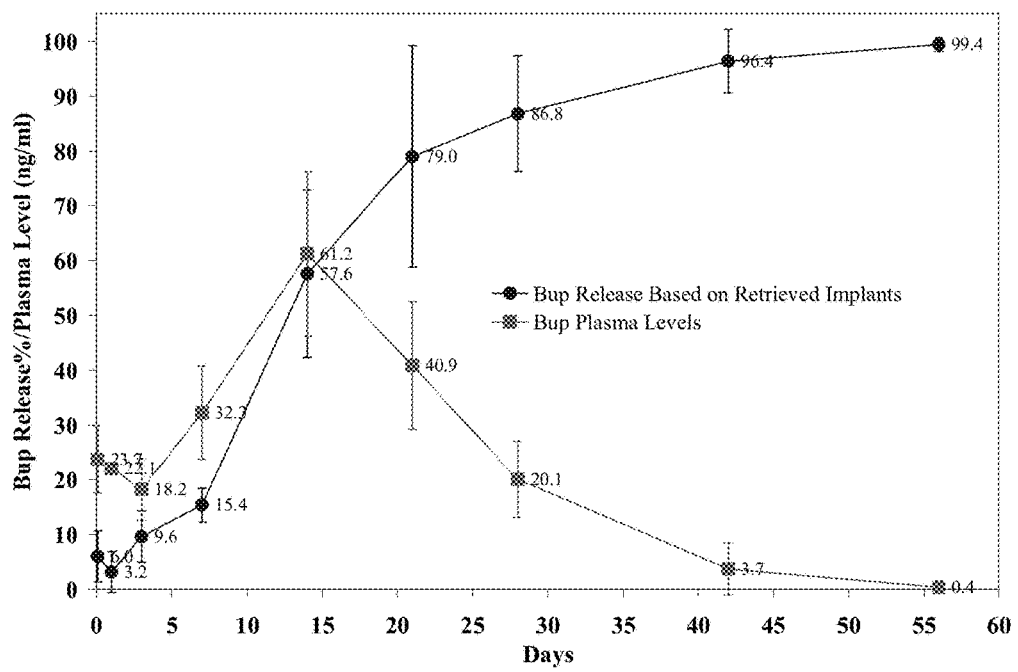
FIG. 1 shows the buprenorphine release and plasma levels after subcutaneous (SC) injection of buprenorphine free base aqueous suspension in rats.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Studies in Rats

Experimental Procedures. All rat preclinical studies were conducted in Sprague-Dawley rats. Five rats per Test Article per time point were injected either intramuscularly or subcutaneously under full anesthesia in the dorsal thoracic (DT) region with approximately 200 mg of the Test Article, described above.

During the course of the study, the animals were observed for overt toxicity and any existing test site abnormalities, including redness, bleeding, swelling, discharge, bruising and Test Article extrusion at the injection site were observed and recorded. In addition, injection weights were recorded at administration and body weights were taken and recorded at administration and at termination. At selected time points, five rats per Test Article were anesthetized and bled (about 5 mL) via cardiac puncture. Blood was collected in labeled potassium ethylenediaminetetraacetic acid tubes. The blood was centrifuged for 10 min at 3000 rpm. The plasma fraction was transferred to labeled 5 mL plastic culture tubes and stored at −86° C. The rat plasma samples were analyzed for buprenorphine concentration using a procedure described below. After blood collection, the rat was sacrificed in a carbon dioxide chamber. The injection site was cut open and the drug residue and the surrounding tissues were carefully removed and placed in a scintillation vial. The vials were stored at −20° C. until analysis. The retrieved drug residue/tissue was analyzed for buprenorphine content using the implant analysis method described below.

Buprenorphine Analysis in Rat Plasma Samples

This procedure was based on that described by Li-Heng Pao et al., Journal of Chromatography B, 746(2000), 241-247.

The High Performance Liquid Chromatography had the following conditions: Mobile Phase: 80/20 acetonitrile/5 mM sodium acetate buffer (pH 3.75); flow rate: 1.2 mL/min; autosampler temperature: room temperature; column temperature: 25° C.; detection: fluorescence (excitation at 215 nm and emission at 355 nm); total run time: 14 min; injection volume: 50 µL; column: Phenomenex Luna Silica (2) 250×4.6 mm, 5 µm; column storage: 100% acetonitrile;

approximate retention time for buprenorphine and the internal standard: 7.9 min and 8.7 min.

Implant Extraction/Analysis Procedure

To the vials containing the retrieved drug residue/tissue, exactly 10 mL of the formulation dissolution solution (90/5/5 acetonitrile/glacial acetic acid/water) was added. The vials were then shaken at about 200 rpm at room temperature on the orbital shaker for at least 2 hours. The vials were then centrifuged at 2500 rpm for 10 minutes. After centrifuge, the vials were carefully removed from the centrifuge. A portion of the supernatant from the vial was transferred into a HPLC vial and if necessary, the transferred solution in the vial was further diluted using the formulation dissolution solution to a suitable concentration for HPLC analysis.

The High Performance Liquid Chromatography had the following conditions: Mobile Phase A: 0.065% sodium octanesulfonic acid and 0.1% trifluoroacetic acid in water; Mobile Phase B: 90/10 acetonitrile/0.065% sodium octanesulfonic acid and 0.1% trifluoroacetic acid in water; flow rate: 1.0 ml/min; autosampler temperature: room temperature; column temperature: 30° C.; detection: 285 run (UV); total run time: 21 min; injection volume: 20 μL; column: Phenomenex Luna C18 250×4.6 mm, 5 μm; column storage: 70/30 acetonitrile/water; each sample run according to the following gradient program:

| Time | Mobile Phase A | Mobile Phase B |
|---|---|---|
| 0 | 100% | 0% |
| 2 | 100% | 0% |
| 16 | 20% | 80% |
| 18 | 0% | 100% |
| 20 | 100% | 0% |
| 21 | 100% | 0% | approximate retention time of buprenorphine: 15.4 minutes.

The standard solution preparation is as follows: standard stock solution was made by dissolving approximately 10 mg buprenorphine in 10 mL 1:1 formulation dissolution solution (90/5/5 acetonitrile/glacial acetic acid/water)/H2O. A series standards ranging from 40 ppm to 500 ppm was diluted with water from the standard stock solution.

Studies in Dogs

Experimental Procedures. All dog preclinical studies were conducted in male beagles with body weight in the range of 8-12 kg. Six dogs per group were injected subcutaneously in the dorsal thoracic region or intramuscularly in the hind legs at a buprenorphine equivalent dose of 60 mg per dog. Exact injection doses were obtained by weighing the injection syringe before and after each injection. After injection, the dogs were bled periodically via jugular vein into EDTA tubes. Plasma samples were then derived and stored in a −80° C. freezer until analysis. Dogs were weighed once daily on blood collection time points. The test sites were evaluated for any abnormalities including redness, bleeding, swelling, discharge, bruising, and TA extrusion on blood collection days. Dogs were also observed post-administration for signs of overt toxicity throughout the entire study period.

Buprenorphine Analysis in Dog Plasma Samples

Plasma samples from dog studies were analyzed for buprenorphine and norbuprenorphine levels using a LC-MS-MS method through a contract analytical service laboratory. The method was developed and validated by the contract service laboratory. It was a proprietary method that employed a liquid-liquid extraction step followed by LC-MS-MS analysis.

1. Preparation of Buprenorphine Free Base Aqueous Suspension

Exactly 3.0 g PEG3350, 0.2 g Tween 80, and 0.9 g sodium chloride were weighed in a 100-ml volumetric flask. Water was added to dissolve and made up to 100 ml. An aliquot of 17.6 g of this aqueous solution was transferred to a 60-ml glass jar, buprenorphine free base (2.4 g) was then weighed in the jar. The jar was further placed in about 20 half inch size Burundum grinding beads. The jar was closed with a lid and then placed on ajar mill to rotate at 60 rpm at room temperature for 24 hours. The buprenorphine suspension was then filled in 1-ml glass ampoules. The filled ampoules were sealed and autoclaved at 121° C. for 15 minutes. Mean buprenorphine free base particle size [d(0.5)] was measured to be 8.3μ by the Malvern Mastersizer 2000 particle size analyzer.

2. Subcutaneous Injection of Micronized Buprenorphine Free Base Aqueous Suspension in Rats.

Formulation: 10% buprenorphine free base suspension in 3% PEG3350 and 0.2% Tween 80 aqueous solution, micronized, subcutaneous injection of 0.2 ml formulation per rat (20 mg bup per rat) (particle size 3.7μ)

Results:

TABLE 1

Buprenorphine release based on retrieved implant analysis

| Time (Day) | Bup Released % | SD |
|---|---|---|
| 0.083333 | 6.0 | 4.7 |
| 1 | 3.2 | 3.7 |
| 3 | 9.6 | 4.7 |
| 7 | 15.4 | 3.1 |
| 14 | 57.6 | 15.2 |
| 21 | 79.0 | 20.2 |
| 28 | 86.8 | 10.6 |
| 42 | 96.4 | 5.8 |
| 56 | 99.4 | 1.3 |

TABLE 2

Buprenorphine plasma levels

| Time (Day) | Bup Level (ng/ml) | SD |
|---|---|---|
| 0.083333 | 23.7 | 6.2 |
| 1 | 22.1 | 1.1 |
| 3 | 18.2 | 5.7 |
| 7 | 32.3 | 8.5 |
| 14 | 61.2 | 15.0 |
| 21 | 40.9 | 11.7 |
| 28 | 20.1 | 6.9 |
| 42 | 3.7 | 4.7 |
| 56 | 0.4 | 0.8 |

FIG. 1 shows the buprenorphine release and plasma levels after subcutaneous (SC) injection of buprenorphine free base aqueous suspension in rats.

3. Intramuscular Injection of Micronized Buprenorphine Free Base Aqueous Suspension in Rats.

Formulation: 13.3% buprenorphine free base suspension in 3% PEG3350, 0.2% Tween 80, and 0.9% sodium chloride aqueous solution, micronized, intramuscular injection of 0.15 ml formulation per rat (20 mg bup per rat) (particle size 10.5μ).

Results:

TABLE 3

Buprenorphine release based on retrieved implant analysis

| Time (day) | Bup Released % | SD |
| --- | --- | --- |
| 0.083333 | 12.3 | 9.9 |
| 1 | 5.9 | 3.1 |
| 4 | 8.0 | 1.3 |
| 7 | 22.7 | 3.4 |
| 14 | 41.9 | 18.0 |
| 21 | 61.0 | 16.7 |
| 28 | 72.8 | 12.2 |
| 42 | 92.0 | 13.0 |
| 56 | 94.8 | 10.5 |
| 69 | 98.0 | 4.0 |

TABLE 4

Buprenorphine plasma levels

| Time (Day) | Bup Level (ng/ml) | SD |
| --- | --- | --- |
| 0.083333 | 26.3 | 17.2 |
| 1 | 25.6 | 6.3 |
| 4 | 39.7 | 15.1 |
| 7 | 45.5 | 13.2 |
| 14 | 22.6 | 10.0 |
| 21 | 19.5 | 8.5 |
| 28 | 27.4 | 8.2 |
| 42 | 15.3 | 8.3 |
| 56 | 1.8 | 1.7 |
| 69 | 1.3 | 1.2 |

Figure 2:
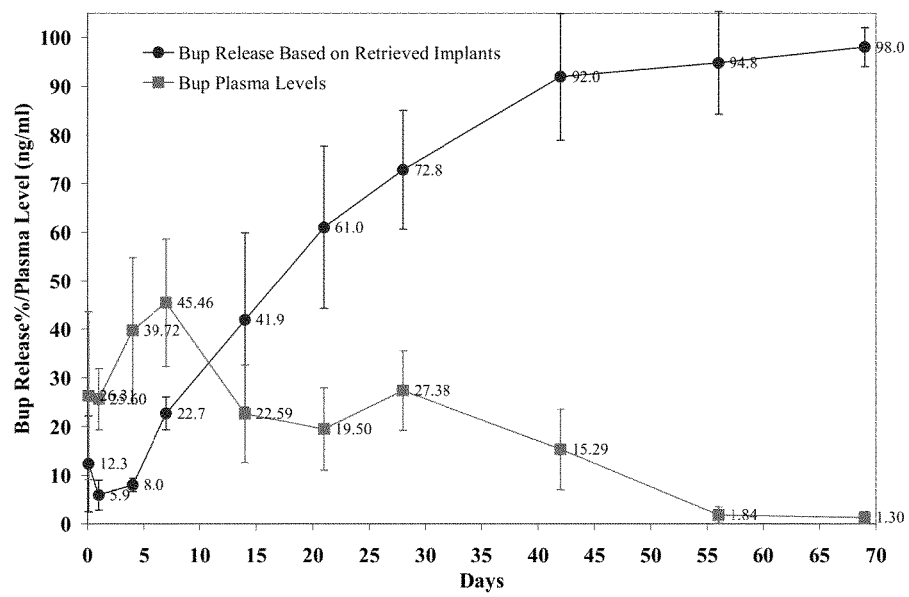
FIG. 2 shows the buprenorphine release and plasma levels after intramuscular (IM) injection of buprenorphine free base aqueous suspension in rats.

FIG. 2 shows the buprenorphine release and plasma levels after intramuscular (IM) injection of buprenorphine free base aqueous suspension in rats.

4. Subcutaneous Injection of Micronized/Larger Particle Size Buprenorphine Free Base Aqueous Suspensions as Well as Buprenorphine Hydrochloride Suspension in Rats) (Particle Size Group I=4.7μ, Group II=40.3μ)

Formulation:

Group I: 10% buprenorphine free base suspension in 0.2% Tween 80 and 0.9% sodium chloride aqueous solution, micronized, subcutaneous injection of 0.20 ml formulation per rat (20 mg bup per rat)

Group II: 10% buprenorphine free base suspension in 0.2% Tween 80 and 0.9% sodium chloride aqueous solution, subcutaneous injection of 0.20 ml formulation per rat (20 mg bup per rat)

Group III: 10% buprenorphine hydrochloride suspension in 0.2% Tween 80 and 0.9% sodium chloride aqueous solution, micronized, subcutaneous injection of 0.20 ml formulation per rat (20 mg bup per rat)

Results:

TABLE 5

Buprenorphine release based on retrieved implant analysis

| Time (Day) | Group I | SD | Group II | SD | Group III | SD |
| --- | --- | --- | --- | --- | --- | --- |
| 0.083333 | 0.1 | 4.5 | 19.6 | 7.8 | 13.9 | 8.5 |
| 1 | 3.9 | 2.1 | 1.4 | 18.6 | 41.4 | 3.7 |
| 3 | 5.1 | 1.2 | 15.4 | 31.4 | 20.1 | 10.3 |
| 7 | 20.5 | 4.4 | 2.6 | 10.4 | 26.3 | 5.4 |
| 14 | 49.5 | 18.0 | 37.7 | 33.5 | 36.7 | 8.7 |
| 21 | 75.0 | 17.1 | 55.9 | 31.2 | 49.6 | 15.5 |
| 28 | 93.8 | 6.6 | 78.5 | 22.3 | 70.7 | 16.6 |
| 42 | 99.9 | 0.1 | 96.6 | 2.1 | 77.0 | 21.8 |

TABLE 6

Buprenorphine plasma levels

| Time (Day) | Group I | SD | Group II | SD | Group III | SD |
| --- | --- | --- | --- | --- | --- | --- |
| 0.083333 | 22.7 | 5.1 | 28.2 | 9.2 | 55.9 | 6.6 |
| 1 | 27.9 | 6.1 | 18.9 | 8.3 | 15.4 | 4.3 |
| 3 | 26.1 | 3.9 | 17.5 | 3.7 | 8.9 | 1.4 |
| 7 | 48.3 | 11.9 | 25.6 | 7.5 | 9.9 | 2.3 |
| 14 | 31.1 | 23.9 | 26.1 | 4.4 | 23.0 | 14.4 |
| 21 | 23.7 | 4.2 | 17.9 | 5.7 | 20.3 | 8.7 |
| 28 | 7.6 | 4.3 | 14.3 | 10.4 | 16.4 | 3.4 |
| 42 | 1.2 | 2.7 | 1.0 | 1.3 | 4.3 | 1.4 |

Figure 3:
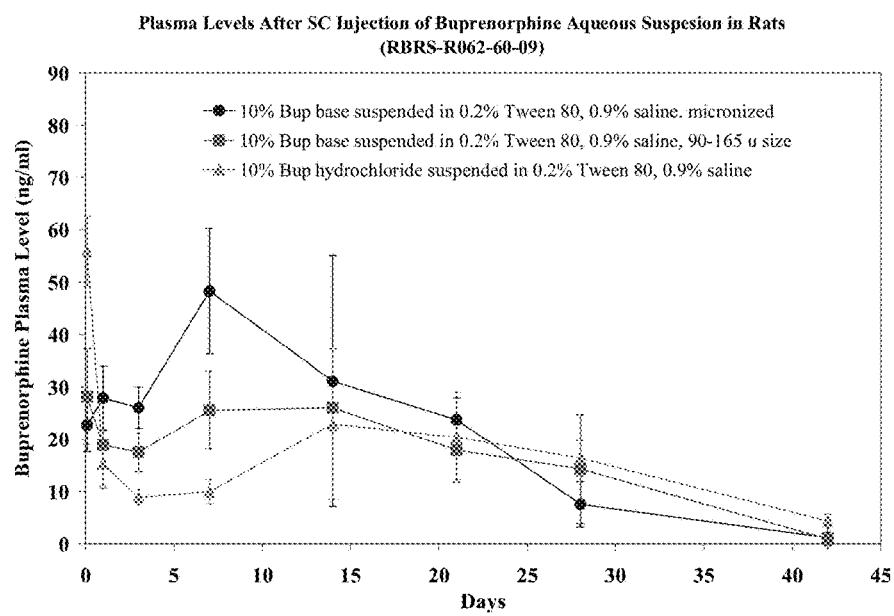
FIG. 3 shows the plasma levels of buprenorphine after subcutaneous (SC) injection of buprenorphine aqueous suspension in rats.

FIG. 3 shows the plasma levels of buprenorphine after subcutaneous (SC) injection of buprenorphine aqueous suspension in rats.

5. Subcutaneous and Intramuscular Injections of Micronized Buprenorphine Free Base Aqueous Suspension in Dogs)

Formulation: 12% buprenorphine free base suspension in 3% PEG3350, 0.2% Tween 80, and 0.9% sodium chloride aqueous solution, micronized, subcutaneous and intramuscular injection of 0.5 ml formulation per dog (60 mg bup per dog) (particle size 8.3μ).

Results:

TABLE 7

Buprenorphine plasma levels after SC injection of bup suspension (Group III)

| Day | BDT8 | TWL5 | SPT8 | TAT8 | WHV8 | XPT8 | Mean | SD |
| --- | --- | --- | --- | --- | --- | --- | --- | --- |
| −4 | * | 0.156 | * | * | * | * | | |
| 1 hour | 3.44 | 5.58 | 13.3 | 7.66 | 10.9 | 5.99 | 7.81 | 3.66 |
| 2 hour | 5.45 | 8.06 | 19.6 | 16.1 | 16.1 | 8.4 | 12.29 | 5.70 |
| 4 hour | 6.04 | 10.1 | 18.5 | 19.5 | 21 | 9.28 | 14.07 | 6.33 |
| 8 hour | 3.51 | 11.9 | 10.6 | 12.6 | 16.5 | 4.25 | 9.89 | 5.06 |
| 1 | 6.64 | 9.2 | 8.3 | 11.5 | 21.9 | 13.1 | 11.77 | 5.47 |
| 3 | 2.84 | 5.8 | 10.9 | 16.1 | 13.4 | 9.4 | 9.74 | 4.87 |
| 7 | 2.79 | 4.1 | 8.62 | 11 | 8.93 | 10.5 | 7.66 | 3.41 |
| 10 | 7.07 | 2.45 | 6.68 | 11.5 | 15.7 | 12.3 | 9.28 | 4.77 |
| 14 | 5.08 | 1.43 | 1.82 | 0.723 | 0 | 1.78 | 1.81 | 1.75 |
| 17 | 5.2 | 1.41 | 1.44 | 0.362 | 0.104 | 0.754 | 1.55 | 1.87 |
| 20 | 5.64 | 1.37 | 1.16 | 0.295 | * | 0.456 | 1.49 | 2.10 |
| 24 | 4.4 | 1.33 | 0.75 | 0.272 | * | * | 1.13 | 1.68 |
| 27 | 1.63 | 1.14 | 0.651 | 0.176 | * | * | 0.60 | 0.67 |

TABLE 7-continued

Buprenorphine plasma levels after SC injection of bup suspension (Group III)

| Day | BDT8 | TWL5 | SPT8 | TAT8 | WHV8 | XPT8 | Mean | SD |
|---|---|---|---|---|---|---|---|---|
| 31 | 0.13 | 1.06 | 0.489 | * | * | * | 0.28 | 0.43 |
| 38 | * | 0.968 | 0.322 | * | * | * | 0.22 | 0.39 |
| 45 | 0.389 | 0.894 | 0.354 | | | | 0.27 | 0.35 |
| 52 | * | 0.767 | 0.232 | | | | 0.17 | 0.31 |
| 66 | * | 0.618 | * | | | | 0.10 | 0.25 |

TABLE 8

Buprenorphine plasma levels after IM injection of bup suspension (Group IV)

| Day | FLV8 | ITV8 | TEV8 | TQT8 | WOT8 | YHT8 | Mean | SD |
|---|---|---|---|---|---|---|---|---|
| −4 | 0.267 | * | * | * | 2.42 | * | | |
| 1 hour | 2.72 | 4.1 | 1.99 | 4.37 | 2.84 | 3.17 | 3.20 | 0.89 |
| 2 hour | 3.73 | 5.38 | 3.18 | 4.15 | 2.99 | 3.87 | 3.88 | 0.85 |
| 4 hour | 4.23 | 6.36 | 2.91 | 5.62 | 3.7 | 5.57 | 4.73 | 1.32 |
| 8 hour | 4.54 | 4.41 | 3.96 | 6.13 | 3.91 | 4.9 | 4.64 | 0.82 |
| 1 | 7.14 | 8.7 | 5.61 | 8.22 | 5.71 | 7.18 | 7.09 | 1.26 |
| 3 | 8.07 | 8.63 | 4.31 | 7.3 | 4.85 | 6.4 | 6.59 | 1.74 |
| 7 | 7.54 | 7.63 | 3.53 | 6.81 | 4.98 | 6.8 | 6.22 | 1.62 |
| 10 | 5.93 | 4.75 | 4.67 | 12.7 | 8.42 | 5.58 | 7.01 | 3.10 |
| 14 | 10.2 | 4.37 | 4.7 | 13.2 | 9.17 | 6.56 | 8.03 | 3.45 |
| 17 | 4.11 | 3.74 | 4.14 | 1.34 | 4.81 | 5.26 | 3.90 | 1.37 |
| 20 | 1.53 | 2.81 | 3.51 | 0.227 | 2.4 | 0.506 | 1.83 | 1.31 |
| 24 | * | 1.92 | 2.32 | * | * | * | 0.71 | 1.10 |
| 27 | * | 1.26 | 1.52 | * | * | * | 0.46 | 0.72 |
| 31 | * | 1.2 | 0.882 | * | * | * | 0.35 | 0.55 |
| 38 | * | 0.797 | 0.511 | * | * | * | 0.22 | 0.35 |
| 45 | * | 1.03 | 0.159 | * | * | * | 0.20 | 0.41 |
| 52 | | 0.598 | * | | | | 0.10 | 0.24 |
| 66 | | 0.355 | * | | | | 0.06 | 0.14 |

{* = BLQ < 0.01}

What is claimed is:

1. A method for treating opioid dependence or pain in a patient in need thereof, the method comprising administering to the patient a therapeutically effective amount of a pharmaceutical composition comprising buprenorphine particles suspended in an aqueous solution comprising:
   (i) polyoxyethylene (20) sorbitan monolaurate, polyoxyethylene (20) sorbitan monooleate, a poloxamer, a phospholipid, or a combination of two or more thereof; and
   (ii) a polyethylene glycol polymer;
   wherein (i) and (ii) are dissolved in the aqueous solution; wherein the buprenorphine particles are buprenorphine free base particles or a pharmaceutically acceptable salt of buprenorphine particles; wherein the buprenorphine particles have an average particle size of less than 100 μm; and wherein the composition does not comprise a polylactide polymer, a polyglycolide polymer, or a copolymer of polylactide and polyglycolide.

2. The method of claim 1, wherein the composition comprises about 5 wt % to about 20 wt % buprenorphine free base particles; wherein the buprenorphine free base particles have an average particle size of less than 50 μm; and wherein (i) comprises polyoxyethylene (20) sorbitan monolaurate, polyoxyethylene (20) sorbitan monooleate, or the combination thereof; and (ii) comprises the polyethylene glycol polymer.

3. The method of claim 2, wherein the polyethylene glycol polymer has a molecular weight between 1,000 and 10,000.

4. The method of claim 1, wherein the buprenorphine particles have an average particle size of less than 20 μm.

5. The method of claim 1, wherein the aqueous solution further comprises a pharmaceutically acceptable salt, a pharmaceutically acceptable sugar, a preservative, or a combination of two or more thereof.

6. The method of claim 1 for treating opioid dependence.

7. The method of claim 1 for treating pain.

8. The method of claim 1, wherein the pharmaceutical composition is administered parenterally and extravascularly to the patient.

9. The method of claim 1, wherein the pharmaceutical composition is administered subcutaneously to the patient.

10. The method of claim 1, wherein the pharmaceutical composition is administered to the patient from about once every 7 days to about once every 30 days.

11. The method of claim 1, wherein the therapeutically effective amount of buprenorphine is from about 0.1 mg to about 10 mg per day.

12. A method for treating opioid dependence or pain in a patient in need thereof, the method comprising administering to the patient a therapeutically effective amount of a pharmaceutical composition to treat the opioid dependence or pain, wherein the pharmaceutical composition comprises buprenorphine particles suspended in an aqueous solution comprising:
   (i) polyoxyethylene (20) sorbitan monolaurate, polyoxyethylene (20) sorbitan monooleate, a poloxamer, a phospholipid, or a combination thereof; and (ii) a polyethylene glycol polymer, a carboxymethylcellulose, a polyvinylpyrrolidone, a polyvinylalcohol, a dextran, or a combination thereof;

wherein (i) and (ii) are dissolved in the aqueous solution; wherein the buprenorphine particles are buprenorphine free base particles or a pharmaceutically acceptable salt of buprenorphine particles; wherein the buprenorphine particles have an average particle size of less than 100 μm; and wherein the composition does not comprise a polylactide polymer, a polyglycolide polymer, or a copolymer of polylactide and polyglycolide.

13. A method for treating opioid dependence in a patient in need thereof comprising subcutaneously administering to the patient an aqueous composition to treat the opioid dependence, wherein the aqueous composition comprises about 5 wt % to about 20 wt % of buprenorphine free base particles suspended in an aqueous solution comprising:
   (i) polyoxyethylene (20) sorbitan monolaurate, polyoxyethylene (20) sorbitan monooleate, or a combination thereof; and
   (ii) a polyethylene glycol polymer;
   wherein (i) and (ii) are dissolved in the aqueous solution; wherein the buprenorphine free base particles have an average particle size of less than 50 μm; and wherein the composition does not comprise a polylactide polymer, a polyglycolide polymer, or a copolymer of polylactide and polyglycolide.

14. The method of claim 13, wherein (ii) is polyoxyethylene (20) sorbitan monooleate.

15. The method of claim 13, wherein the buprenorphine free base particles have an average particle size of less than 20 μm.

16. The method of claim 13, wherein the polyethylene glycol polymer has a molecular weight between 1,000 and 10,000.

17. The method of claim 13, wherein the polyethylene glycol polymer has a molecular weight of about 3350.

18. The method of claim 12 to treat opioid dependence.

* * * * *